United States Patent [19]
Dodd et al.

[11] Patent Number: 5,258,385
[45] Date of Patent: Nov. 2, 1993

[54] β-CARBOLINE-DERIVED COMPOUNDS, LAMCHART BENZODIAZEPINE-RECEPTOR LIGANDS, HAVING AN INVERSE AGONIST AND ANTAGONIST EFFECT ON BENZODIAZEPINES, AND DRUGS CONTAINING THEM

[75] Inventors: Robert Dodd; Pierre Potier; Jean Rossier, all of Paris; Gilbert Dorey, Chaville; Laurent Dubois, Gif-Sur-Yvette; Lia Prado de Carvalho, Paris, all of France

[73] Assignee: Centre National de la Recherche Scientifique (CNRS), Paris, France

[21] Appl. No.: 834,399

[22] Filed: Feb. 12, 1992

[30] Foreign Application Priority Data

Feb. 12, 1991 [FR] France .................. 91 01595

[51] Int. Cl.$^5$ ............... C07D 213/81; A61K 31/435
[52] U.S. Cl. ................................ 514/287; 546/64
[58] Field of Search ............... 546/64; 514/285, 287

[56] References Cited

U.S. PATENT DOCUMENTS 3,644,384 2/1972 Schulenberg .................. 546/64

FOREIGN PATENT DOCUMENTS 0237467 3/1987 European Pat. Off. ........... 546/64

OTHER PUBLICATIONS

Mann et al., J. of Chem. Soc., Part XIII, pp. 3830-3833, 1959.

Primary Examiner—C. Warren Ivy
Assistant Examiner—Zinna N. Davis
Attorney, Agent, or Firm—Cushman, Darby & Cushman

[57] ABSTRACT

The invention relates to novel β-carboline-derived compounds which are benzodiazepine-receptor ligands having an inverse agonist and antagonist effect on benzodiazepines. These compounds are of the formulae:

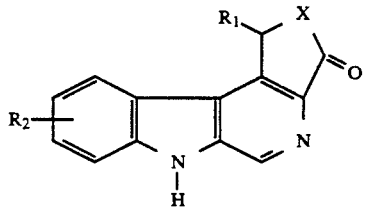

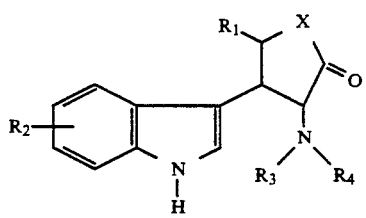

in which:
X is O, S,

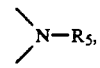

or alternatively,

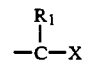

represents the radical —N(R$_6$)—C(=O)—CH$_2$—X,
R$_1$ is a hydroxyl, alkoxy or alkyl radical substituted by a hydroxyl or alkoxy radical,
R$_2$ is a hydrogen atom or an alkyl, hydroxyl, alkoxy, acyloxy or benzyloxy radical, it being possible for said radicals to be optionally substituted,
R$_3$, R$_4$, R$_5$ and R$_6$ are chosen from a hydrogen atom or an alkyl radical optionally substituted by a hydroxyl, alkoxy or alkoxycarbonylmethyl radical, as well as the corresponding tetrahydro derivatives of β-carboline and the quaternary ammonium salts or derivatives of these pharmaceutically acceptable compounds.

9 Claims, No Drawings

β-CARBOLINE-DERIVED COMPOUNDS, LAMCHART BENZODIAZEPINE-RECEPTOR LIGANDS, HAVING AN INVERSE AGONIST AND ANTAGONIST EFFECT ON BENZODIAZEPINES, AND DRUGS CONTAINING THEM

The invention relates to novel β-carboline-derived compounds which are benzodiazepine-receptor ligands, having an inverse agonist and antagonist effect on benzodiazepines, and to the pharmaceutical compositions containing these compounds.

It also relates to the methods for preparing said compounds and to the novel compounds which may be optionally used to carry out these preparation methods.

1,4-Benzodiazepines (for example valium) constitute a category of drugs widely prescribed because of their anxiolytic, anticonvulsant, sedative-hypnotic and muscle-relaxant activities. The mechanism of action of benzodiazepines has long remained misunderstood until specific binding sites (or "receptors") were identified for these molecules on the neuronal membranes of the central nervous system. The physiological importance of these receptors has been demonstrated by the existence of a good correlation between, on the one hand, the degree of affinity of the various benzodiazepines for the receptor (measured by displacement of a radioactive benzodiazepine) and, on the other hand, their therapeutic efficacy.

Similarly, it has been found that some β-carbolines behave like agonists of the receptor and of benzodiazepines.

Thus, Abecarnil, developed by Schering laboratories as an anxiolytic,

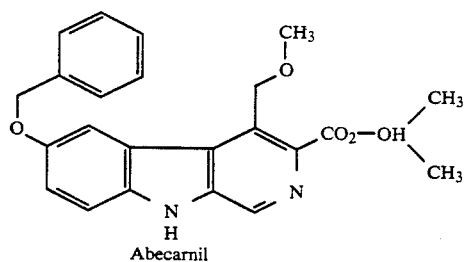
Abecarnil

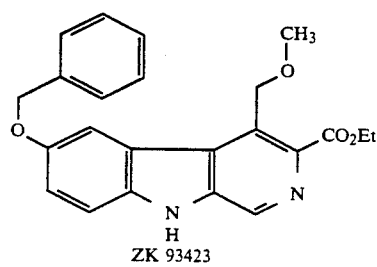
ZK 93423

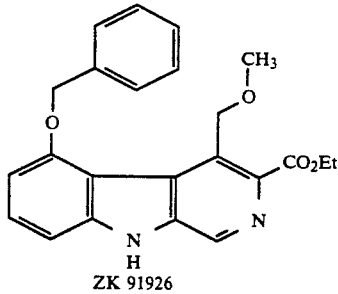
ZK 91926 is undergoing clinical trials. Other related β-carbolines such as ZK 93423 and ZK 91296 also possess properties similar to those of diazepam in vivo (anxiolytic, anticonvulsant and the like).

While searching for an endogenous ligand of the benzodiazepine receptor, Braestrup et al. (Proc. Natl. Acad. Sci., USA, 77, 2288–2292, 1980) identified a molecule, the ethyl ester of β-carboline-3-carboxylic acid (β-CCE), extracted from human urine, which binds with a very good affinity to the central receptors for benzodiazepines ($IC_{50}=4$ nM, in vitro, rat brain). In contrast, β-CCE possesses in vivo pharmacological effects opposed to those of benzodiazepines. Thus, β-CCE is a proconvulsant in mice which facilitates the convulsions caused by other agents such as pentylenetetrazole.

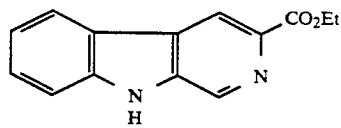

The term "inverse agonist" is now used to denote those benzodiazepine-receptor ligands which posses activities which are completely or partially opposed to those of benzodiazepines.

The therapeutic advantage of β-carbolines is found at several levels. Thus, the team, which is the author of the present invention, was the first to demonstrate that such molecules (for example, the β-CCM below),

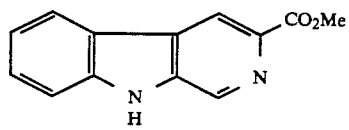

which are benzodiazepine-receptor inverse agonists, have a positive effect on learning and memory (Venault et al., Nature, 321, 864–866, 1986). Although β-CCM could not be tested in man for its promnesic effects due to its highly convulsant activity, other analogs (for example, ZK 93426) have demonstrated their capacity to improve learning and information retention in man (Duka et al. Psychopharmacology, 93, 421–427, 1987).

ZK 93426

β-Carbolines containing a γ- or δ-lactone or a γ- or δ-lactam ring have also been described. These compounds exhibit an average affinity for the benzodiazepine receptor (Neef G. et al. J. Chem. Soc. Chem. Comm., 366, 1982 and Neef, G. et al. Heterocycles, 20, 1295-1312, 1983).

As a result, one of the aims of the present invention is to propose novel compounds exhibiting an affinity for the benzodiazepine receptor while possessing an inverse agonist and antagonist effect.

Another aim of the present invention is to propose novel therapeutic compositions which are useful in particular in the treatment of nervous disorders.

Another aim of the present invention is to propose novel therapeutic compositions having a positive effect on learning and memory and capable of being used for the treatment of cognitive problems such as for example in Alzheimer's disease.

The invention therefore relates primarily to the compounds of formulae:

I

II in which:
X is an oxygen or a sulfur atom or a divalent radical $NR_5$,
or, alternatively, the radical $$-\overset{R_1}{\underset{|}{C}}-X-$$

represents the radical $$-N(R_6)-\overset{O}{\overset{\|}{C}}-CH_2-X-,$$

$R_1$ is chosen from hydroxyl or alkoxy radical radicals substituted by a hydroxyl or alkoxy radical, $R_2$ is a hydrogen atom or a radical chosen from alkyl, hydroxyl, alkoxy, acyloxy or benzyloxy radicals, it being possible for said radicals to be optionally substituted, $R_3$, $R_4$, $R_5$ and $R_6$ are chosen from a hydrogen atom or an alkyl radical optionally substituted by a hydroxyl, alkoxy or alkoxycarbonylmethyl radical, as well as the corresponding tetrahydro derivatives of β-carboline and the quaternary ammonium salts or derivatives of these pharmaceutically acceptable compounds.

In the present description, alkyl, alkoxy or acyloxy radicals preferably have 1 to 6 carbon atoms and may be linear or branched (preferably linear).

Moreover, some compounds possess one or more asymmetric centers. They may therefore exist in one or more optically active forms. In this case, the invention comprises said optically active forms of these compounds.

Chlorides, hydrochlorides, tartrates and fumarates may be mentioned among the salts.

According to a first preferred variant, the compounds according to the invention are of the formula I in which:

$R_1$ and $R_2$ have the same meaning as above and X is an oxygen atom or a divalent radical $N-R_5$. Advantageously, $R_1$ is an alkyl radical substituted in $\alpha$ by a hydroxyl or alkoxy radical, or R is a hydroxyl or alkoxy radical and/or $R_2$ is a hydrogen atom. Still more advantageously, $R_1$ is a hydroxymethyl radical.

According to a second preferred variant, the compounds are of the formula II in which: $R_1$ and $R_2$ have the same meaning as before, $R_3$ and $R_4$ are a hydrogen atom and X is an oxygen atom or a divalent radical $N-R_5$. Still preferably, $R_1$ is an alkyl radical substituted in $\alpha$ by a hydroxyl or alkoxy radical, or $R_1$ is a hydroxyl or alkoxy radical and/or $R_2$ is a hydrogen atom. Still more advantageously, $R_1$ is a hydroxymethyl radical.

According to a third preferred variant, the compounds are of the formula:

in which:
$R_2$, $R_5$ and $R_6$ have the same meaning as given above.
Preferably, $R_5$ and $R_6$ are chosen from a hydrogen atom or an alkyl radical and/or $R_2$ is a hydrogen atom.

According to a fourth variant, the invention relates to compounds of formula (I) which are tetrahydro derivatives of the first and third variants.

Preferably, the compounds according to the invention are chosen from the following compounds in an optically active or racemic form:
1,12-dihydro-2-methylindolo[3',2':4,5]pyrido-[2,3-f]-1H,3H,6H-1,4-diazepine-3,12-dione;
10-ethoxybutanolide[2,3-b]-β-carboline,
10-methoxybutanolide[2,3-b]-β-carboline, ethyl 10-hydroxy-2-oxopyrrolidin-2-one[3,4-b]-β-carboline-5-carboxylate,
10-hydroxymethylbutanolide[2,3-b]-β-carboline,
3-hydroxymethyl-4-(5-benzyloxy-3-indolyl)-5-amino-gamma-lactone.

The invention also relates to drugs consisting of one of the compounds according to the invention, as has just been described above, and the pharmaceutical compositions containing at least one of these drugs and an acceptable carrier. These drugs and compositions are useful for the medical or veterinary treatment of certain disorders linked to the functioning of the nervous system.

These drugs and compositions are particularly intended to be used in combination with benzodiazepines in order to compensate for the adverse effects due to the use of the latter. These compounds themselves also improve learning and information retention in man.

These drugs and compositions may thus be advantageously intended to be used in an effective therapy against degenerative diseases of the nervous system, in particular dementias of the Alzheimer type.

The pharmaceutical compositions are in particular formulated to be ingested orally or to be injected. However, other presentations may also be envisaged within the framework of the present invention.

The dosage will partly depend on the disease to be treated as well as on its seriousness and also on the type of individual (weight, age).

A dosage ranging from 0.1 mg/kg to 20 mg/kg may be advantageously envisaged.

The invention also relates to preparation methods enabling the compounds according to the invention to be obtained.

A method for preparing the compounds of formula (I) in which X is an oxygen atom, $R_2$ has the same meaning as above, $R_1$ is a hydroxyl or alkoxy radical, consists in transetherifying and unblocking in one step a compound of formula:

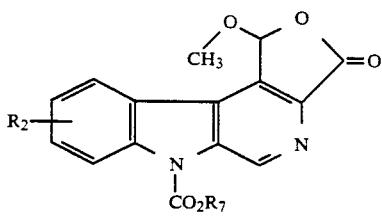

III $R_7$ a $C_1$–$C_6$ alkyl radical, in the presence of the corresponding alcohol or water. This step is preferably carried out in the presence of a reducing metal such as sodium.

The compound of formula III may be obtained according to the following scheme:

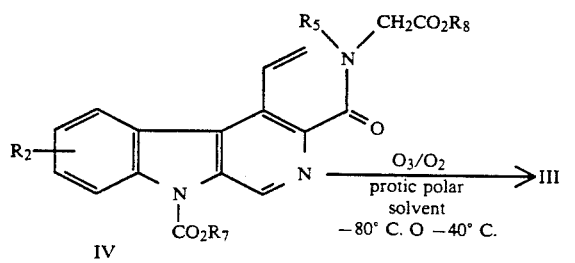

$R_5$ being different from H,
$R_6$ being a $C_1$–$C_6$ alkyl radical.

The compound of formula IV may be obtained according to the following scheme:

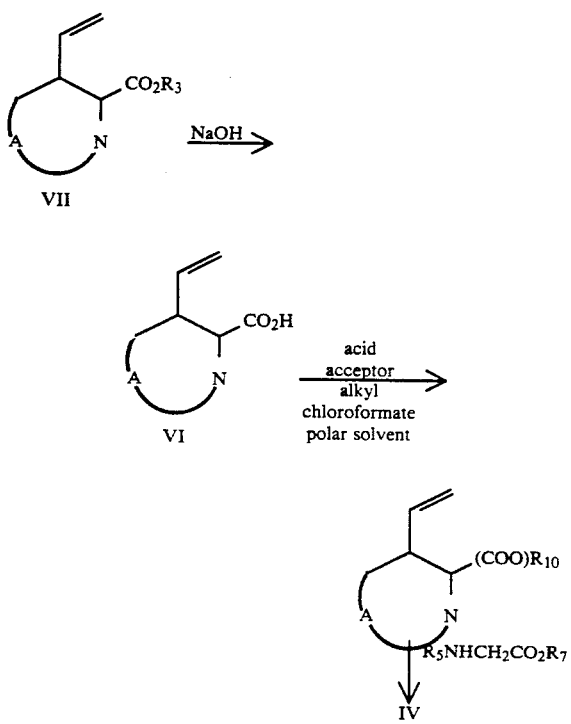

$R_9$ and $R_{10}$ being chosen from alkyl radicals, A being the residue of the β-carboline skeleton of I.

Thus, the subject of the invention is also a novel preparation of the compounds of formula V and VI according to the scheme above.

A method of preparing the compounds of formula I in which X is an oxygen atom, $R_2$ has the same meaning as above, $R_1$ is a methyl radical substituted by a hydroxyl or alkoxy radical, consists in oxidizing a compound of formula IV or of formula:

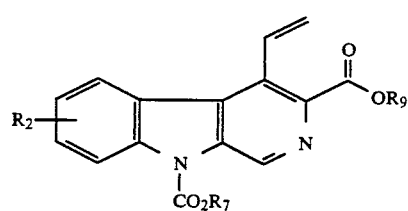

VIII $R_9$ being an alkyl radical, for example using osmium tetroxide, followed by unblocking of the nitrogen atom and optionally by etherification using the corresponding alcohol or vice versa.

The synthesis of the compound of formula VIII is obtained by treating the compound of formula VII (Neef et al. Heterocycles 20, 1295 (1983)) with a chloroformic alkyl and triethylamine in THF:

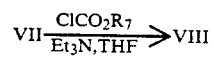

Another method consists in reacting a compound of formula VII or of formula:

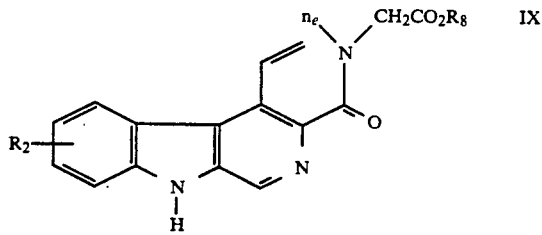

with osmium tetroxide and optionally etherifying using the corresponding alcohol.

The starting compounds are prepared in the same manner as above by, for example, unblocking the nitrogen of the pyrrole ring.

A method for preparing the compounds of formula (I) in which X is a divalent radical N-R$_5$, R$_1$ is a hydroxyl or alkoxy radical, consists in converting a compound of formula IV (where R$_5$ is the hydrogen atom) to a compound of formula:

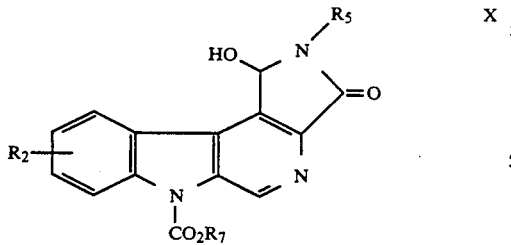

by ozonolysis, optional exchange of the group CH$_2$CO$_2$R$_6$ of the lactam with a radical R$_5$=alkyl, then unblocking the nitrogen atom of the pyrrole by the action of an alcohol in the presence of sodium and then optionally etherifying the compound obtained.

The compound of formula IV is obtained as indicated above.

A method for preparing the compounds of formula (I), in the case where X is N(R$_6$)—C(=O)—CH-2—N—R$_5$, R$_2$ has the same meaning as above, consists in cyclizing in acid medium a compound of formula:

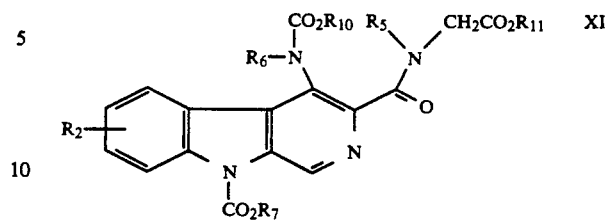

R$_{10}$ and R$_{11}$ being chosen from alkyl radicals (preferably t-Bu for R$_{10}$), and then in carrying out the unblocking step according to the method above. The starting product of formula XI may be obtained according to the following scheme:

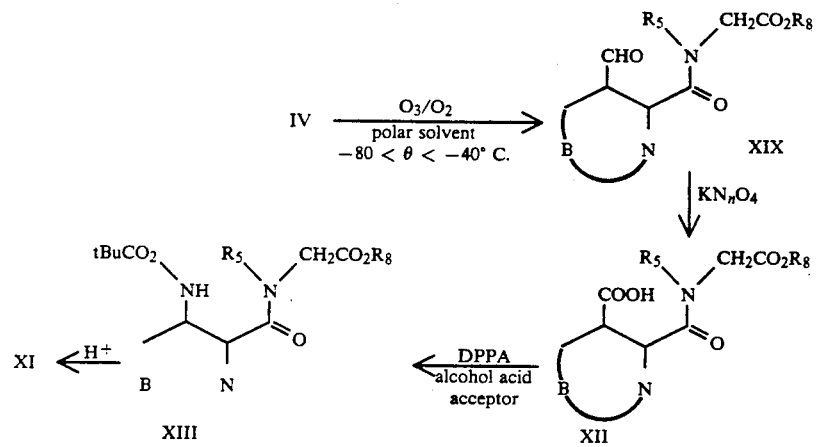

B being the β-carboline residue of IV.

The reaction from IV to XIX is similar to that leading to the compound III and most often leads to a mixture of two species which can be purified by a subsequent separation.

A process for preparing the compounds of formula (II) in which X is an oxygen atom, R$_1$ is an alkyl radical substituted in α by a hydroxyl or alkoxy radical, R$_2$, R$_3$ and R$_4$ have the same meaning as before, consists in heating a compound of formula:

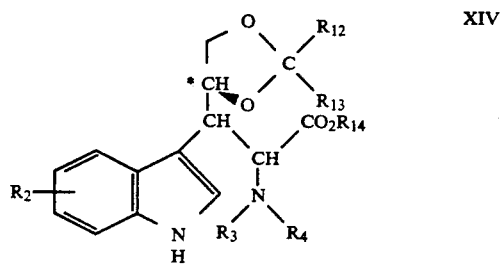

R$_{12}$, R$_{13}$ and R$_{14}$ being chosen from a hydrogen atom or alkyl radicals in an aqueous acetic medium.

The compound of formula XIV may be obtained according to the following method, given by way of example:

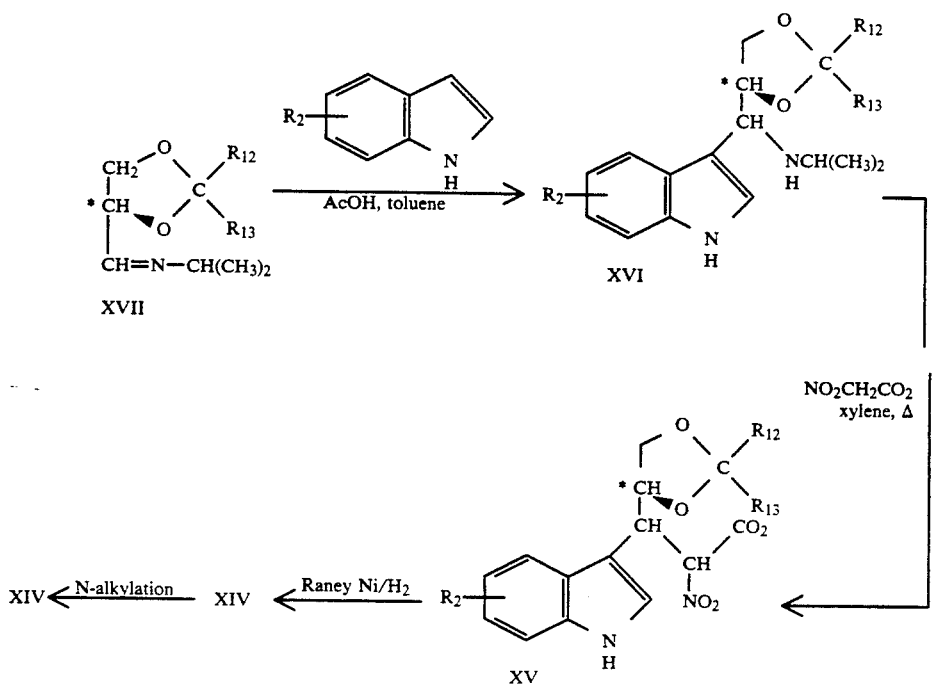

A method for preparing the compounds of formula (I), in which tetrahydro-β-carboline derivatives are involved, and $R_1$ is a methyl substituted by hydroxyl or alkoxy and X=O, consists in reacting the compounds of formula II with formaldehyde in the presence of an aprotic polar solvent.

Similarly, it is possible to obtain these compounds by reacting the compounds of formula:

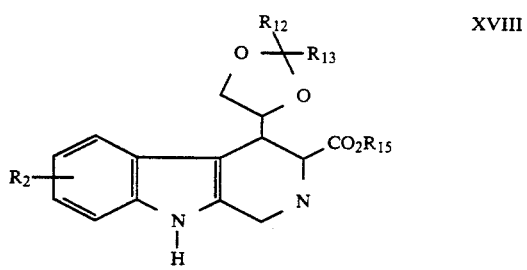

$R_{15}$ being an alkyl radical, in aqueous acetic medium.

The compounds of formula XVIII are obtained by reaction of formaldehyde, in toluene while heating, with the compound of formula XIV (where $R_3$ and $R_4$ are a hydrogen atom).

It is also possible to obtain the compounds of formula (I), where X=O and $R_1$ is an alkyl radical substituted in α by a hydroxyl radical, by aromatization of the compound of formula XVIII described above and then by cyclization in aqueous acetic medium. This family of compounds may also be prepared by aromatization of the corresponding tetrahydro compounds.

The invention also relates to stereoselective preparation methods which make it possible to obtain compounds according to the invention possessing one or more asymmetric carbons.

These methods are particularly advantageous in the case of the compounds of formula (I) in which X=O, $R_1$ is alkoxy, hydroxyl, hydroxymethyl or alkoxymethyl.

Such a method is given below by way of example.

STEREOSELECTIVE SYNTHESIS OF THE R AND S ISOMERS OF 10-HYDROXYMETHYLBUTANOLIDE2.3-b]-β-CARBOLINE

The synthesis is illustrated by the following reaction sequence:

Aldimine reacts on the indole ring in the presence of acetic acid at 5° C. in toluene to give the expected gramine (Scheme 4). Displacement of the isopropylamine group is performed by action of ethyl nitroacetate in xylene under reflux. The nitrated derivative is isolated with a yield of 75% after chromatography.

scheme 4

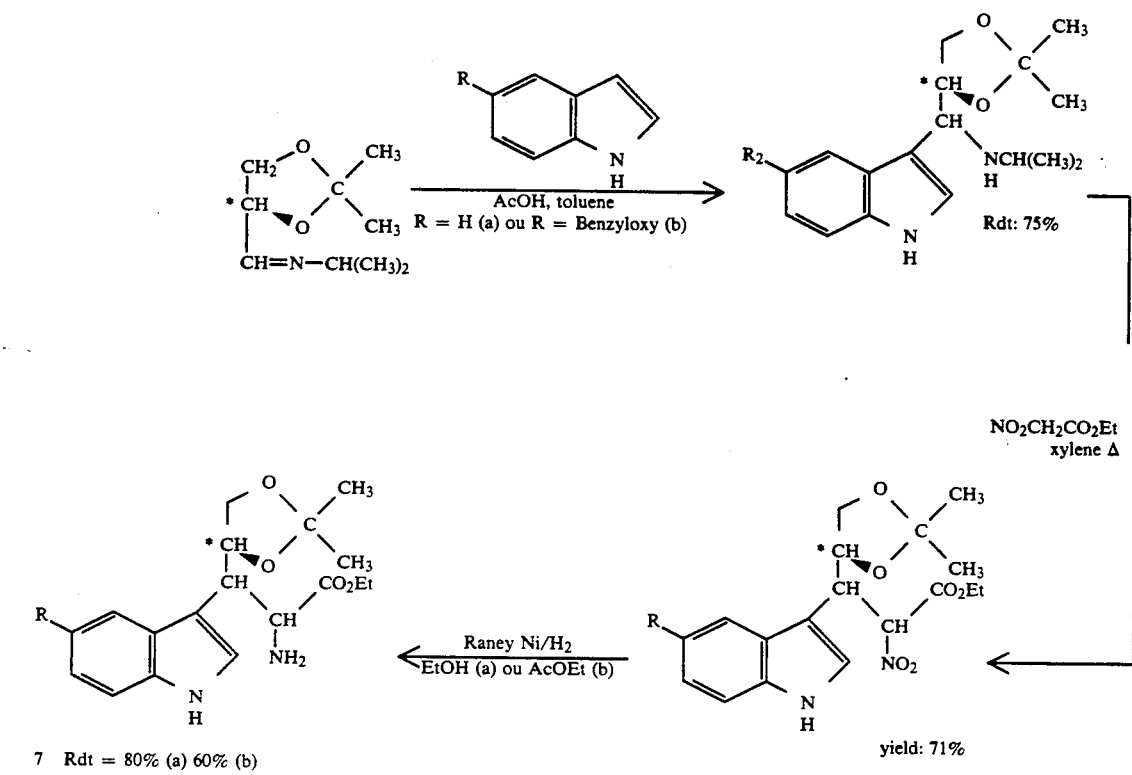

Reduction of the nitro group was carried out selectively in the presence of Raney nickel under a hydrogen atmosphere in ethyl acetate, without debenzylation in the case of the benzyloxy derivative. The resulting amines were then cyclized to aminolactone 2 or converted to tetrahydro-β-carboline 3 according to a described, known mechanism (scheme 5).

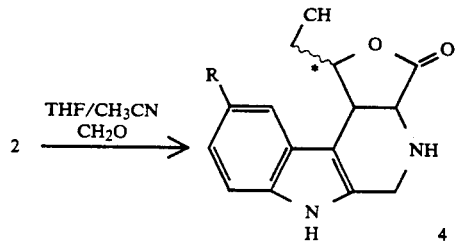

scheme 5

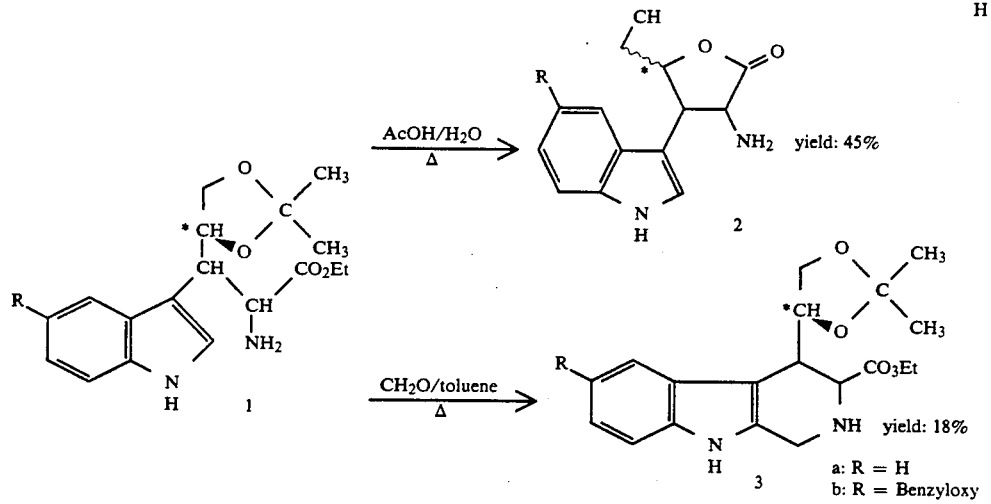

The aminolactone 2 may be converted to β-carboline 4 using known mild conditions.

The tetrahydro-6²-carbolines 2 and 4 are aromatized in the presence of sulfur under reflux in DMSO. In the case of 2, the β-carboline 3 is obtained, which is cyclized in the presence of acetic acid and water to form stereoselectively the desired lactones 5(R=H) and 6 (R=OCH₂C₆H₅). The tetrahydro-β-carboline 4 gives directly, under these conditions, the desired optically pure lactone (R isomer).

Some other compounds, whose method of preparation is not explicitly described, are obtained in a manner known to a person skilled in the art.

The following examples illustrate the methods for preparing some of the compounds according to the invention.

EXAMPLE 1 scheme 6

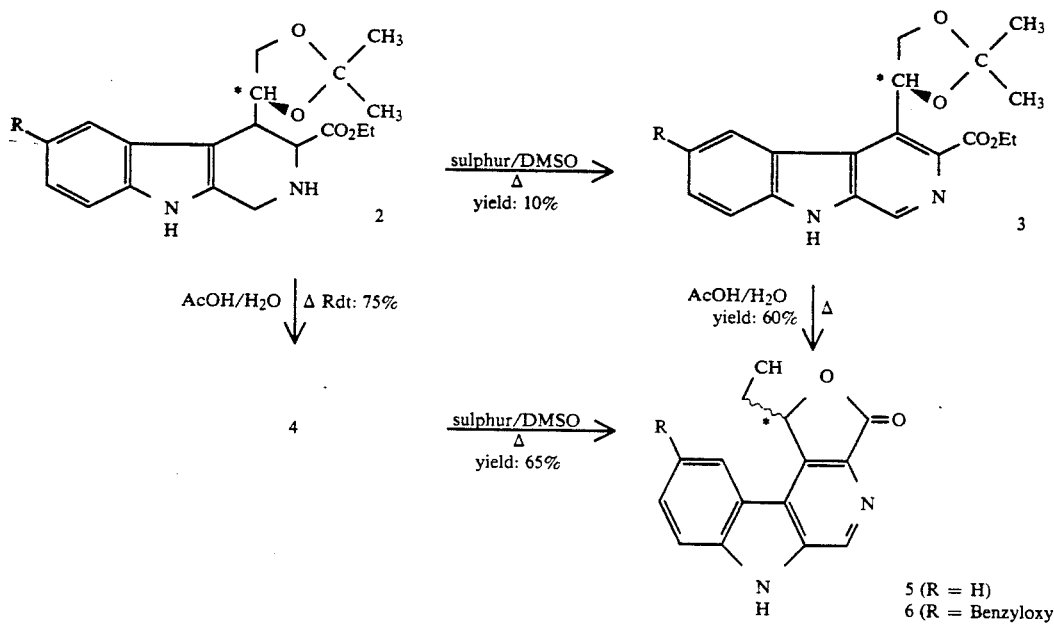

The S isomer of 10-hydroxymethylbutanolide-[2,3-b]-β-carboline (5-5) was obtained from L-glyceraldehyde-acetonide 7 according to the syntheses routes described above. The compound 7 is itself synthesized from L-ascorbic acid 8 according to a known "one-pot" method (in one phase).

10-Ethoxybutanolide[2,3-b]-β-Carboline (Compound No. 1)

285 mg (0.70 mmol) of β-carboline of formula IV in which $R_2$=H, $R_5$=Me, $R_7$=$R_6$=Et, are dissolved in a mixture of dichloromethane (15 ml) and anhydrous methanol (5 ml). The reaction mixture is cooled to −78° scheme 7

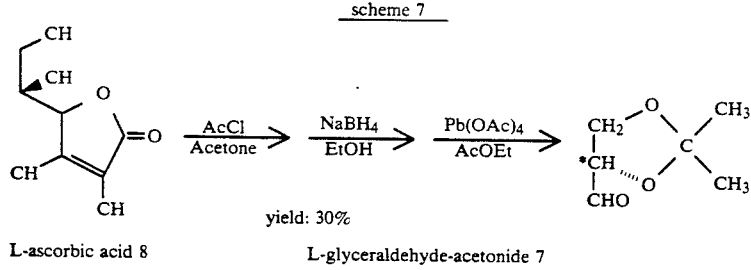

L-ascorbic acid 8    L-glyceraldehyde-acetonide 7

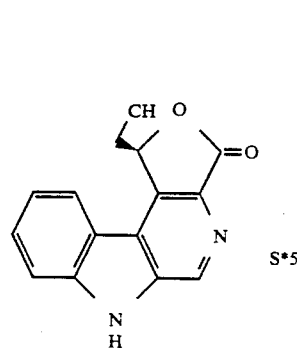

S*5

C. using an ethanol and solid carbon dioxide bath. An oxygen and ozone mixture is introduced for 1 h 50 min (complete disappearance of the starting product in TLC) and then a nitrogen stream is bubbled in for 5 min. 0.4 ml (3.38 mmol) of trimethylphosphite is then introduced and the mixture is allowed to stand for 1 hour at room temperature. After evaporating the solvents under reduced pressure, the yellow oily residue is purified by high-performance liquid chromatography (graft silica: methanol-water; 7:3). The following compounds are isolated: a beige solid (96 mg; 0.29 mmol) which is the compound N-ethoxycarbonyl-10-methoxybutanolide[2,3-b]-$\beta$-carboline which melts at 180° C. with decomposition (yield 42%) and an aldehyde (15 mg, 0.036 mmol) which is N-ethylethoxycarbonyl-N-methyl-(9-ethoxycarbonyl-4-formyl)-$\beta$-carboline-3-carboxamide which melts at 113-114° C., with a yield of 5%.

The $\gamma$-lactone obtained (37 mg; 0.112 mmol) is deprotected in the presence of 5 ml of ethanol and 1.3 mg of sodium at room temperature with stirring, neutralized with a small amount of acetic acid and then the reagents and solvent are evaporated under reduced pressure. The oily residue is taken up in dichloromethane; the resulting precipitate is filtered and then rinsed with water to remove the inorganic salts. 26.8 mg (0.10 mmol of compound no. 1) are isolated after drying.

Yield: 88%; m.p. >310° C. with decomposition.

EXAMPLE 2

Preparation of
10-Methoxybutanolide2,3-b]-$\beta$-Carboline (Compound No. 2)

5.2 mg (0.02 mmol) of the deprotected compound no. 2 are isolated from 8.7 mg of the protected compound no. 1 (0.03 mmol) and 4 ml of methanol containing 0.4 mg of sodium, under the same experimental conditions as those described in Example 1;

Yield: 63%; m.p.=314-315° C. with decomposition.

EXAMPLE 3

10-Hydroxymethylbutanolide[2.3-]-$\beta$-Carboline Compound No. 3)

700 mg (1.71 mmol) of the compound of formula IV above are dissolved in a mixture of dioxane (75 ml) and water (30 ml) and a catalytic amount of solid osmium tetroxide is added. The mixture is stirred for 30 min and then 2 g (9.35 mmol) of sodium periodate are introduced. The mixture is stirred at room temperature, protected from light, for 21 hours. The inorganic salts formed during the reaction are then filtered and rinsed with dioxane. The solvent is then evaporated under reduced pressure and the residue is taken up in ethyl acetate and washed with a saturated solution of sodium chloride. After drying over sodium sulfate, evaporation and purification on a silica column [dichloromethane-ethanol (8:0.2)], 20 mg (0.06 mmol) of the protected compound with a melting point of between 202° and 204° C. (yield 5%), 382 mg (0.93 mmol) of the aldehyde described in Example 1, and 88 mg (0.21 mmol) of the unreacted starting product are isolated.

6.6 mg (0.026 mmol) of the deprotected compound (No. 3) are isolated from 11.7 mg of this compound (0.036 mmol) and 2.5 ml of ethanol containing 0.6 mg of sodium, under the same experimental conditions as those described in Example 1.

Yield: 72%; m.p.=278-280° C. with decomposition.

EXAMPLE 4

N-Ethylethoxycarbonyl-10-Hydroxy-2-Oxopyrrolidin-2-One3,4-b]-$\beta$-Carboline (Compound No. 4)

75 mg (0.19 mmol) of $\beta$-carboline of formula IV, in which $R_2$ and $R_5$=H, and $R_7$ and $R_6$=Et, are dissolved in a mixture of dichloromethane (6 ml) and anhydrous methanol (2 ml). The reaction mixture is cooled to −78° C. using an acetone and solid carbon dioxide bath. An oxygen and ozone mixture is then introduced for 5 min (the solution becomes bluish in color) and then a nitrogen stream is bubbled in for 2 min. 100 $\mu$l (0.84 mmol) of trimethylphosphite are then introduced and the mixture is allowed to stand for 2 h 30 min while allowing the temperature to reequilibrate to around 20° C. The solvents are evaporated under reduced pressure to give an oily residue which is chromatographed on silica [dichloromethane-ethanol (8:0.2)]. The tetracyclic compound 3 (65 mg; 0.16 mmol) is isolated in the form of white crystals.

Yield: 86%; m.p.=194-196° C.

1.7 mg (0.21 mmol) of the deprotected compound are isolated from 17.4 mg of the compound obtained (0.044 mmol) and 3 ml of ethanol containing 0.5 mg of sodium, under the same experimental conditions as those described in Example 1.

Yield: 49%; m.p.=240° C. (compound no. 4)

EXAMPLE 5

1.12-Dihydro-2-Methylindolo-[3',2':4,5]pyrido-[2,3-f]-1H,3H,6H-1,4-Diazepine-3,12-Dione (Compound No. 5)

Stage 1: Preparation of N-methyl-N-ethylethoxy-carbonyl-(9-ethoxycarbonyl-4-carboxylic acid)-$\beta$-carboline-3-carboxamide Route A: Oxidation Using Meta-Chloroperbenzoic Acid.

The 4-formyl-$\beta$-carboline from Example 1 (27 mg; 6.57 mmol) is dissolved in a mixture of tetrahydrofuran and water (5:1). The solution is cooled using an ice cold water bath and placed under a nitrogen stream. 14.5 mg of meta-chloroperbenzoic acid are then introduced into the reaction mixture and the mixture is stirred at 4° C. for 24 hours. The solvents are then evaporated under reduced pressure and the residue chromatographed on silica (toluene-ethanol (8:3)) 10.8 mg (2.54 mmol) of carboxylic acid are recovered.

Yield 39%; Rf: 0.06 [SiO₂, toluene-ethanol (8:2)].

Route B: Oxidation Using Potassium Permanganate 145 mg (0.353 mmol) of the 4-formyl-$\beta$-carboline above are dissolved in a mixture containing 30 ml of acetone and 6 ml of water. 139 mg (0.879 mmol) of potassium permanganate, previously dissolved in 2 ml of water, are added and the mixture is stirred at room temperature for 3 hours. A slight excess of formaldehyde is then added into the reaction mixture and stirred until the violet color of the permanganate has completely disappeared. The manganese dioxide formed is removed by filtration on sintered glass, rinsed with acetone and the filtrate evaporated under reduced pressure. The yellow residue is taken up in dichloromethane and placed at 4° C. for 2 hours. The white solid which precipitates in this medium is filtered and then washed with ethanol. 127 mg (0.297) of the expected carboxylic acid are thus isolated in the form of a very fine white powder. Yield 84%.

Stage 2: Preparation of N-methyl-N-ethylerhoxycarbonyl-[9-ethoxycarbonyl-N-(4-tert-butoxycarbonyl)]-β-carboline-3-carboxamide The acid from stage 1 (127 mg; 0.30 mmol) is suspended in 20 ml of distilled tert-butanol. The mixture is placed under a nitrogen stream and then 53 μl of distilled triethylamine (0.39 mmol) and 77 μl of diphenoxyphosphorylazide (0.36 mmol) are introduced. The reaction mixture is then heated at boiling temperature for 9 hours and stirred at room temperature for 20 hours. 38.2 mg (0.08 mmol) of the expected product are isolated after evaporation of the reagents and solvents under reduced pressure and chromatography of the residue on silica (toluene-ethanol, 8:1).

Yield: 25%; Rf: 0.29 [SiO$_2$, toluene-ethanol (8:1)].

Stage 3: Preparation of N-ethylethoxycarbonyl-(9-ethoxycarbonyl-4-amino)-β-carboline-carboxamide.

The β-carboline obtained in stage 2 (50 mg: 0.1 mmol) is dissolved in 3 ml of anhydrous dichloromethane. 19 μl (0.2 mmol) of trifluoroacetic acid are added to the solution and the mixture is stirred at room temperature for 18 hours. After this period, excess trifluoroacetic acid is neutralized with solid sodium bicarbonate. The reaction mixture is then filtered and evaporated under reduced pressure. The residue, chromatographed on silica (toluene-ethanol, 8:0.2), leads to the expected amine (6 mg) in the form of a white solid.

Yield: 15%; Rf: 0.10 [SiO$_2$, toluene-ethanol (8:1)].

Stage 4: Preparation of 1,12-dihydro-6-ethoxycarbonyl-2-methylindolo[3',2':4,5]pyrido[2,3-f]-1H,3H, 6H-1,4-diazepine-3,12-dione The acid obtained in stage 1 (68 mg: 0.16 mmol) is suspended, under nitrogen, in 6 ml of dry toluene, and the mixture is stirred at room temperature. 45 μl (0.21 mmol) of diphenoxyphosphorylazide and 33 μl (0.24 mmol) of distilled triethylamine are introduced and stirring is maintained until the starting product has completely disappeared (TLC: SiO$_2$, toluene-ethanol, 8:2). The reagents and solvents are then evaporated under reduced pressure and the solid residue is taken up in a mixture of acetic acid (3 ml) and water (3 ml). The reaction mixture is refluxed for 1 h 30 min. After this period, the mixture is diluted with ethyl acetate and it is neutralized with an aqueous solution of sodium bicarbonate (10%). After extraction, the organic phase is dried, filtered and evaporated to give an oil (50 mg) which is chromatographed on silica (toluene-ethanol, 8:2). The expected β-carbolinodiazepinone (10.4 mg: 0.03 mmol) is obtained in the form of a white solid.

Yield 12%; Rf: 0.30[SiO$_2$, toluene-ethanol (8:2)].

Stage 5: Preparation of 1,12-dihydro-2-methylindolo[3',2':4,5]pyrido[2,3-f]-1H,3H,6H-1,4-diazepine-3,12-dione (compound no. 5)

The hybrid obtained in stage 4 (10 mg; 0.028 mmol) is dissolved in 2 ml of ethanol containing a catalytic amount of sodium. The reaction solution is stirred at room temperature for 2 h 30 min (complete disappearance of the starting product). The mixture is then neutralized with a small amount of acetic acid and then the reagents and solvents are evaporated under reduced pressure. The oily residue is taken up in dichloromethane; the resulting precipitate is filtered and then rinsed with water to remove the inorganic salts. 5 mg (0.018 mmol) of the deprotected hybrid (compound no. 5) are isolated, after drying, in the form of a white solid.

Yield: 64%; m.p.=260°-270° C. with decomposition.

The examples below illustrate the biological properties of the compounds according to the invention.

BIOLOGICAL ACTIVITY

The affinity of these novel ligands towards the benzodiazepine receptor was determined by in vitro binding tests using preparations of rat brain cortical membranes (according to the method of Rehavi et al., Eur. J. Pharmacol. 78, 353, 1982). These affinities, indicated by the IC$_{50}$ values (the substance concentration required to displace 50% of $^3$H-flunitrazepam from its recognition sites on the benzodiazepine receptor), are in the nanomole range (cf table below). However, one molecule is noticeable, δ-hydroxymethyllactone 5, which possesses an affinity of 0.18 nM. This affinity is 20 times higher than that of β-CCE (4 nM) and 100 times higher than that of diazepam (20 nM). The abovementioned lactone therefore represents the most improved β-carboline known so far for the benzodiazepine receptor.

The pharmacological profile was then determined.

The effect of the lactone on the benzodiazepine receptor expressed was first expressed, using the corresponding messenger RNA, in xenopus oocyte. When the lactone (10$^6$ M) is administered simultaneously with a 10$^5$ M solution of gamma-aminobutyric acid (GABA), no increase or decrease was observed in the current generated in the oocyte by the latter molecule. The lactone therefore behaves, in this test, like an antagonist of the benzodiazepine receptor. Furthermore, the lactone (10$^6$ M) inhibits substantially the increase in the current generated by a receptor agonist such as diazepam (10$^6$ M).

The antagonist properties of the lactone were also assessed in vivo in mice. When administered to mice, the derivative (5 mg/kg,·sc) produces no effect on their behavior, being neither convulsant nor sedative. In contrast, the sedation caused by diazepam (7.5 mg/kg, sc) is completely avoided by administering the compound (5 or 10 mg/kg, sc).

TABLE

Affinities of various synthesized molecules for the benzodiazepine receptor in vitro (rat brain, displacement of $^3$H-flunitrazepam at 0° C.)

| Compound | IC$_{50}$ nM |
|---|---|
| 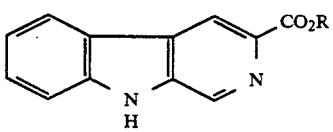 | 4 |
| 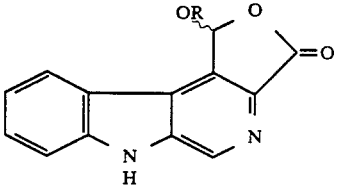 | R = CH$_3$  12<br>R = C$_2$H$_5$  20 |

TABLE-continued

Affinities of various synthesized molecules for the benzodiazepine receptor in vitro (rat brain, displacement of $^3$H-flunitrazepam at 0° C.)

| Compound | | IC$_{50}$ nM |
|---|---|---|
| 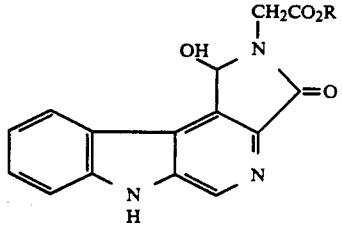 | | 70 |
| 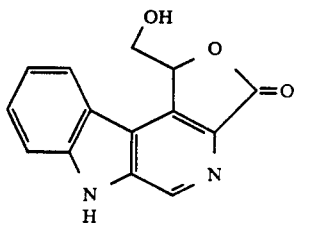 | R,S— | 0,18 |
| 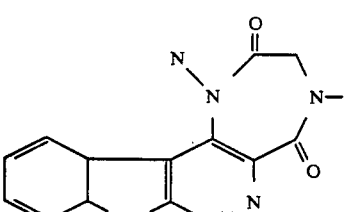 | | 65 |
| 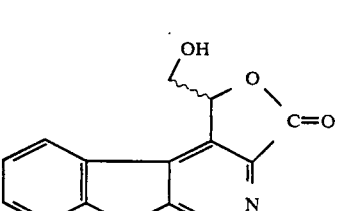 | S—<br>R— | 0,54<br>0,25 |
| 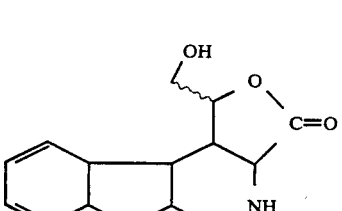 | S—<br>R— | 750<br>1000 |
| 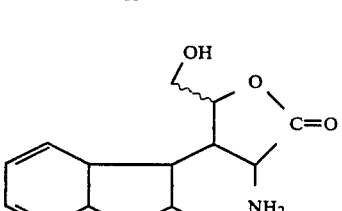 | S—<br>R— | 220<br>300 |
| 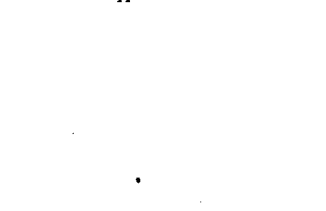  :R = Benzyloxyl | R— | 270 |
| 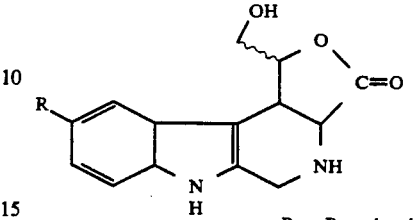  :R = Benzyloxyl | R— | 77 |

We claim:

1. A compound of formula,

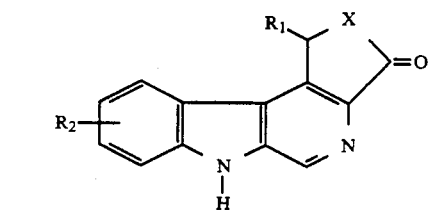

in which:

X is an oxygen or a sulfur atom or a divalent radical NR$_5$, or, alternatively, the radical

represents the radical

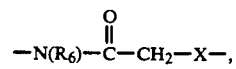

R$_1$ is chosen from hydroxyl or alkoxyl radicals or alkyl radicals substituted by a hydroxyl or alkoxyl radical, R$_2$ is a hydrogen atom or a radial chosen from alkyl, hydroxyl, alkoxy, acyloxy or benzyloxy radicals, R$_5$ and R$_6$ are chosen from a hydrogen atom or an alkyl radical optionally substituted by a hydroxyl, alkoxy or alkoxycarbonylmethyl radicals, and the corresponding tetrahydro compounds of formula I and the pharmaceutically acceptable quaternary ammonium chlorides, tartrates and fumarates of these compounds.

2. The compound as claimed in claim 1, which is of the formula I:
in which X is an oxygen atom or the divalent radical

and $R_1$ and $R_2$ have the same meaning as in claim 1.

3. The compound as claimed in claim 2, wherein $R_1$ is an alkyl radicals substituted in $\alpha$ by a hydroxyl or alkoxy radical, or $R_1$ is a hydroxyl or alkoxy radical.

4. The compound as claimed in claim 3, wherein $R_1$ is a hydroxymethyl radical.

5. The compound as claimed in claim 2, wherein $R_3$ is a hydrogen atom.

6. The compound as claimed in claim 1, wherein $R_2$ is a hydrogen atom.

7. A tetrahydro compound of formula:

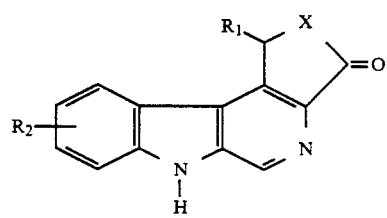

in which the substituents $R_1$, $R_2$ and X have the same meaning as in claim 1.

8. A compound as claimed in claim 1 wherein it is chosen from the following compounds:
1,12-dihydro-2-methylindolo[3',2':4,5]pyrido-[2,3-f]-1H,3H,6H-1,4-diazepine-3,12-dione;
10-ethoxybutanolide[2,3-b]-β-carboline,
10-methoxybutanolide[2,3-b]-β-carboline,
ethyl 10-hydroxy-2-oxopyrrolidin-2-one[3,4-b]-β-carboline-5-carboxylate,
10-hydroxymethylbutanolide[2,3-b]-β-carboline,
3-hydroxymethyl-4-(5-benzyloxy-3-indolyl)-5-amino-gamma-lactone.

9. A pharmaceutical composition consisting of a compound of formula,

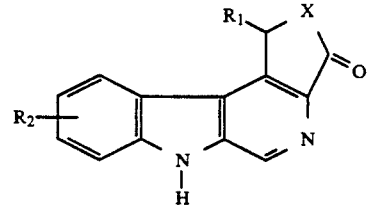

in which:
X is an oxygen or a sulfur atom or a divalent radical $NR_5$, or, alternatively, the radical

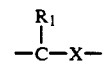

represents the radical

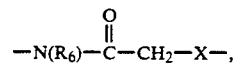

$R_1$ is chosen from hydroxyl or alkoxyl radicals or alkyl radicals substituted by a hydroxyl or alkoxyl radicals, $R_2$ is a hydrogen atom or a radical chosen from alkyl, hydroxyl, alkoxy, acyloxy or benzyloxy radicals, $R_5$ and $R_6$ are chosen from a hydrogen atom or an alkyl radical optionally substituted by a hydroxyl, alkoxy or alkoxycarbonylmethyl radical, and the corresponding tetrahydro compounds of formula I and the pharmaceutically acceptable quaternary ammonium chlorides, tartrates and fumarates of these compounds; and optionally, a pharmaceutically acceptable carrier.

* * * * *